United States Patent [19]

Huch et al.

[11] 4,114,602
[45] Sep. 19, 1978

[54] PROCESS AND ARRANGEMENT FOR DETERMINING THE PERFUSION FACTOR OF A GAS IN A SAMPLE

[75] Inventors: Albert Huch, Marbach, Marburg; Dietrich Werner Lübbers, Dortmund, both of Fed. Rep. of Germany

[73] Assignee: L. Eschweiler & Co., Kiel, Fed. Rep. of Germany

[21] Appl. No.: 704,295

[22] Filed: Jul. 12, 1976

[30] Foreign Application Priority Data

Jul. 10, 1975 [DE] Fed. Rep. of Germany ....... 2530834

[51] Int. Cl.² .............................................. A61B 5/00
[52] U.S. Cl. .................................. 128/2 E; 128/2.1 E
[58] Field of Search ........................... 128/2 E, 2.1 E; 204/195 B; 128/2 A, 2 G, 2 L, 2 R, 2.05 V; 204/195 P, 1 P

[56] References Cited

U.S. PATENT DOCUMENTS 3,918,434   11/1975   Lubbers et al. .............. 128/2.1 E X

OTHER PUBLICATIONS

Pfluegers Archiv 273, 199–209/1961, Kanzow.
Clark, Trans. Amer. Soc. Art. Int. Org. 2, 41 (1956).
Luebbers, Pfluegers Arch. 271 431/1960.
Doctoral Thesis of Renate Huch, delivered in 1971 in Marburg, Germany, p. 7.

Primary Examiner—Robert W. Michell
Assistant Examiner—Michael H. Thaler
Attorney, Agent, or Firm—Michael J. Striker

[57] ABSTRACT

A process and an arrangement for determining the perfusion factor of a gas in a sample, particularly of oxygen dissolved in blood flowing through biological tissue, includes measuring the amount of gas diffused from the sample by means of a polarographic cell which comprises a reference electrode having a heat conductive surface which is adapted to be placed in heat-transmitting relationship over a portion of the sample, and a sensor electrode in electrolytic contact with the reference electrode so as to generate a signal indicative of the amount of gas being diffused from the sample portion. A heating unit comprising a high frequency generator to establish a high frequency field in the sample is also provided for heating the sample diathermically to a desired temperature. The temperature of the sample is thereupon detected by a temperature sensor attached to the heat conducting surface, which is operative to generate a control signal for the heating unit which is operative to maintain the temperature of the reference electrode at a substantially constant value. The amount of heat furnished by the heating unit to the reference electrode which is equivalent to the flow of blood stream is thereupon measured so that the perfusion factor of the gas is determinable from the aforementioned measured amounts of gas diffused from the sample portion and of heat supplied to the same.

9 Claims, 2 Drawing Figures

PROCESS AND ARRANGEMENT FOR DETERMINING THE PERFUSION FACTOR OF A GAS IN A SAMPLE

BACKGROUND OF THE INVENTION

The present invention relates to a process and an arrangement for determining the perfusion factor of a gas in a sample, and in particular to a process and an arrangement which determines the perfusion factor of oxygen which is dissolved in blood flowing through biological tissue.

It is already known to provide a device for polarographically measuring the amount of oxygen being diffused from the bloodstream of a sample. It is also known to provide a separate device for diathermically heating the sample portion and measuring flow of the blood stream through the sample by the heat supplied to the latter. For example, see Pfluegers Archiv 273,199–209/1961, Kanzow. However, in order to accurately determine the perfusion factor of the oxygen which is a function of both of these measurements, it is necessary to simultaneously measure both of these quantities at the same location.

It will be understood that the prior-art teaching of having separate devices is very disadvantageous since it is necessary for one to correctly position one of the devices, take a measurement, and — after removal of the first device from the sample portion — to correctly position the other device on the sample, and thereupon take another measurement. This interchange of devices must take place quickly inasmuch as the physiological measuring conditions vary as a function of time.

It is also known in the prior art U.S. Pat. No. 3,918,434 to measure the perfusion factor by using an electrical resistive wire heater which heats up a metallic member that is placed over the sample portion. However, this prior-art apparatus has the disadvantage that all of the heat flows through the interface between the metallic member and the sample portion. This means that the prior-art devices are strongly subject to rapid and frequent fluctuations in the contact resistance of the metallic member at the interface by virtue of the changing physiological conditions which, of course, leads to measurement errors.

SUMMARY OF THE INVENTION

Accordingly, it is an object of the present invention to overcome the disadvantages of the prior art.

More particularly, it is an object of the invention to provide a structurally integrated single arrangement which reliably measures the perfusion factor of a gas in a sample.

Still more particularly, it is an object of the present invention to provide such an improved arrangement and process whereby the amount of gas being diffused from the sample and the amount of heat supplied to the same may be simultaneously measured.

Another object of the present invention is to generate heat in the sample instead of in the probe to avoid heat conducting problems between the tissue and the heat conducting surface of the sample.

Another object of the present invention is to provide a light-weight, easy to handle, portable arrangement for measuring perfusion factor.

In keeping with the above objects, and with others which will become apparent hereinafter, one feature of the invention resides, briefly stated, in a combination in a process and an arrangement for determining the perfusion factor of a gas in a sample, particularly of oxygen dissolved in blood flowing through biological tissue, which comprises means for polarographically measuring the amount of gas diffused from the sample by utilizing a polarographic cell which comprises a reference electrode having a heat-conductive surface adapted to be placed in heat-transmitting relationship over a portion of the sample, and a sensor electrode in electrolytic contact with said reference electrode so as to generate a signal indicative of the amount of gas being diffused from the sample portion. Heating means comprising a high frequency generator are electrically connected with the reference electrode so as to heat the sample portion to a desired temperature by the high frequency field. In addition, a temperature sensor is electrically connected with the reference electrode and the heating means for detecting the temperature of the reference electrode so as to generate a control signal for said heating means to maintain the temperature of the reference electrode at a substantially constant value. Moreover, means for measuring the amount of heat furnished by the heating means to the reference electrode and thus to the sample portion are provided so that the perfusion factor of the gas may be determined from said measured amount of gas diffused from the sample portion and of heat supplied to the same.

Another feature of the invention is that the heating means comprises a generator for establishing a high-frequency electric field intermediate the reference electrode and a metallic casing which is spaced from and which surrounds the reference electrode. Thus, the high-frequency field is located exteriorly of the sensor electrode and does not interfere with its gas-measuring function. This is a signficant consideration inasmuch as the signal generated by the polarographic cell lies in the nanoampere and microvolt region.

Thus, in accordance with the invention, both measurements of heat supplied to the sample portion and of the gas diffused from the same can be measured simultaneously at the same location by a single arrangement, thus eliminating a major source of error in the prior-art devices. Moreover, inasmuch as the polarographic cell is covered by a membrane which contacts the sample portion and which has a rather low heat capacity, measurement errors are even further substantially reduced because only this interface must be maintained at a substantially constant temperature.

Moreover heat supply errors by variation of the heat conducting at the interface of sample and probe will not occur since the heat is generated inside the sample.

In accordance with another feature of the invention, the reference electrode may be electrically heated by auxiliary heating means in order to improve the heat transmission at the interface.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENT

Figure 1:
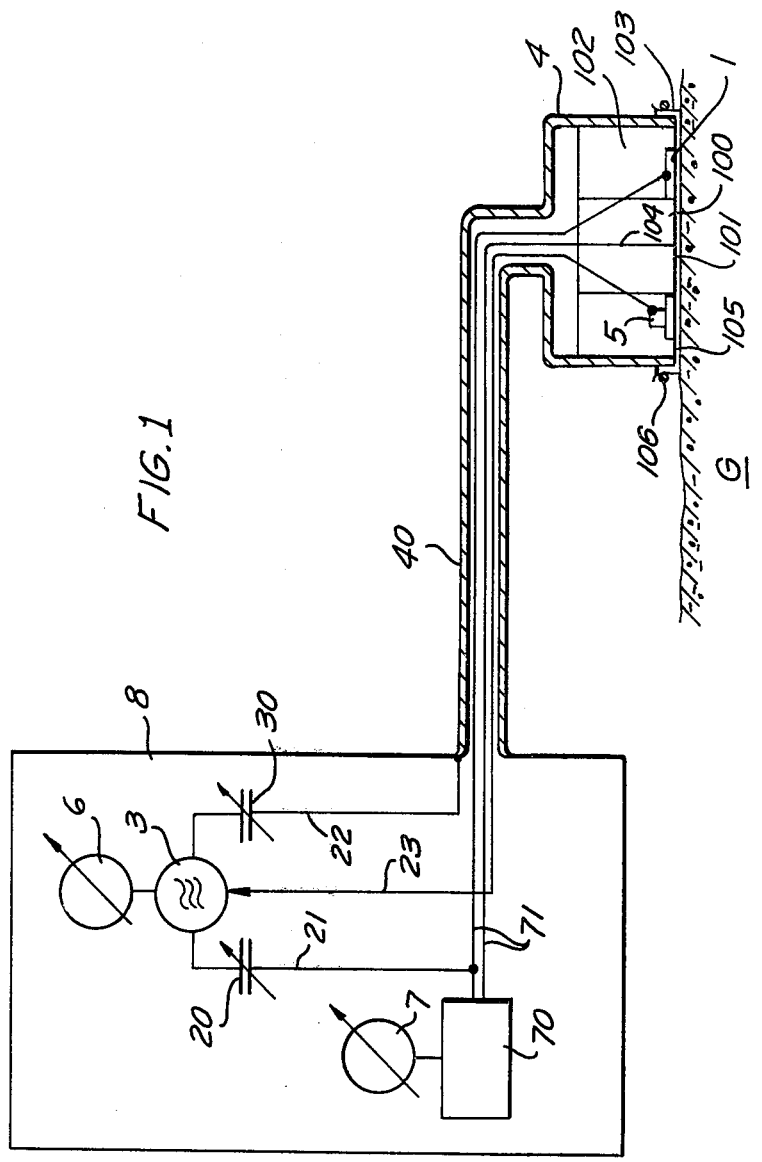
FIG. 1 is a diagrammatic view, partially in section, of a currently preferred embodiment according to the present invention.
Figure 2:
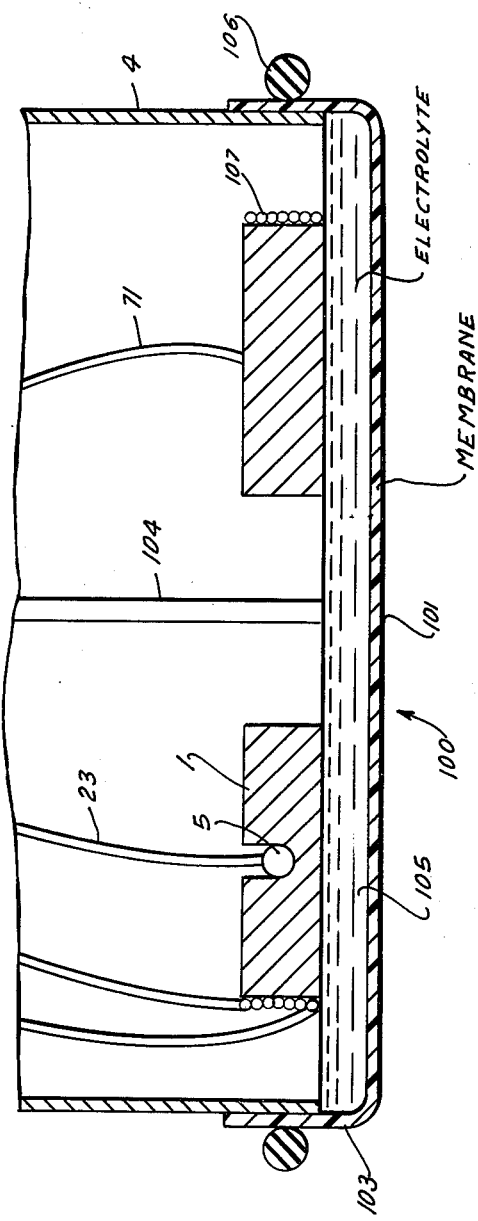
FIG. 2 is a enlarged view of a part of the structure depicted in FIG. 1.

Referring firstly to the currently preferred embodiment illustrated in FIGS. 1 and 2, it will be seen that the sample whose perfusion efficiency factor or rate is to be measured is identified by the letter G. The sample G may be any human or animal tissue wherein blood-filled capillaries are present. It is the perfusion factor of the gas, for example oxygen, which is contained in the bloodstream which is to be determined by the illustrated arrangement. It will be appreciated that the perfusion factor of gases other than oxygen in the bloodstream may also be determined by using the disclosed arrangement and process. For the sake of providing a clear description of the invention, the arrangement and the process will be described in connection with the determination of oxygen being diffused from the bloodstream through the exterior skin of human tissue. However, it is to be expressly understood that this description is not intended to be self-limiting in any manner.

Since perfusion factor is a function of two quantities, namely the amount of oxygen gas being diffused from the sample and the flow of the blood stream in the latter, these two quantities are to be measured. The amount of oxygen gas is measured by a polarographic cell 100 which includes a reference electrode 1 having a heat-conductive surface which is adapted to be placed in heat-transmitting relationship over a portion of the sample G. Reference electrode or the non-polarized electrode 1 is constituted of silver chloride coated silver material. Reference electrode 1 is annular-shaped and surrounds sensor electrode 104, i.e. the polarized electrode, which is generally constituted of platinum. The pair of electrodes 1, 104 are sealed in spaced electrically-insulating relationship within a glass carrier 102. The oxygen-sensing end portion of sensor electrode 104 and the lower surface of reference electrode 1 are located in a common plane and are both in contact with an electrolyte 105, such as potassium chloride and water.

Covering means or gas-permeable membrane 103, preferably constituted of Teflon, is juxtaposed from the aforesaid common plane so as to form a space therewith, and the permeable membrane 103 serves to retain the electrolyte 105 in this space. Sealing means 106 prevents the electrolyte 105 from leaking out of this space.

The polarographic cell 100 or measuring head, as thus comprised, has a lower surface 101 which contacts the surface of the sample tissue portion G at the interface.

It is through this lower surface 101 of the membrane 103 that oxygen from the sample portion G diffuses and thereupon contacts the electrodes 1, 104. In accordance with the teachings of Clark, Trans. Amer. Soc. Art. Int. Org. 2,41 (1956), and Luebbers, Pfluegers Arch, 271, 431/1960 and R. Huch, page 7 of her doctoral thesis delivered in 1971 in Marburg, Germany, an electrical current path is generated through the electrolyte 105 and an electrical signal is generated which is indicative of the amount of oxygen gas being diffused from sample portion G. This electrical signal is conveyed by a pair of electrical conductors 71 towards an electrical device 70 which contains the source of applied voltage for the electrodes. Device 70 also contains means for amplifying the electrical signal and for conveying the latter to the diagrammatically-illustrated oxygen-measuring instrument 7 where the amplified signal is finally indicated.

Heating means 3 are provided in order to heat the sample portion G to the desired temperature at which the perfusion factor is to be determined. Preferably the heating means 3 comprises a generator which is operative for diathermically establishing a high-frequency oscillating electrical field adjacent the sample portion G. A metallic screen or casing 4 surrounds the polarographic cell 100 and is spaced at a distance from the reference electrode 1 so as to be electrically insulated therefrom. The output of the generator 3 is respectively connected to the reference electrode 1 and the casing 4 by means of a pair of electrical conductors 21 and 22. Specifically, conductor 21 is connected to the conductor 71 which is electrically connected with the reference electrode 1; and the conductor 22 is connected to a tubular extension portion 40 of the casing 4. Thus, in operation, a high-frequency field is established intermediate the reference electrode 1 and the casing 4.

Sensing means 5 is electrically connected with reference electrode 1 and is operative for sensing the temperature of the latter and thereby for generating a control signal which is conveyed by conductor 23 to generator 3. The control signal is operative for controlling the output of the generator 3 so as to maintain the temperature of the reference electrode 1 at a substantially constant value.

A diagrammatically-illustrated measuring instrument 6 measures the output of the generator 3, i.e. instrument 6 indicates the amount of heat furnished by the generator 3 to the reference electrode 1 and thus to the sample portion. Thus, both of the aforementioned quantities from which the perfusion factor of the oxygen gas is determinable have been obtained.

It is preferable to adjust the output of generator 3 to produce electrical oscillations at a frequency of approximately 500 MHz. Adjusting means 20 and 30 for the adjustment of the wave resistance of the conductors are respectively provided in conductors 21 and 22 in order to tune the wave resistance of the conductors 21 and 22.

A portable housing 8 contains the measuring instruments 6 and 7, the generator 3, and the adjusting elements 20 and 30. The housing 8 is connected with the tubular extension portion 40 which is preferably flexible in order to readily position the polarographic cell 100 and the casing 4 on the sample portion.

According to a preferred embodiment of the invention, the platinum electrode 104 is cylindrical-shaped and has a diameter of approximately 12 microns. Furthermore, the Teflon membrane 103 which covers the electrodes is formed with a thickness of approximately 15 microns.

In order to reduce the heat-transmission requirement at the interface between surface 101 and sample portion G, the reference electrode 1 can be additionally heated by auxiliary heating means 107.

It will be understood that each of the elements described above, or two or more together, may also find a useful application in other types of constructions differing from the types described above.

While the invention has been illustrated and described as embodied in a process and arrangement for determining the perfusion factor of a gas in a sample, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspect of this invention.

What is claimed as new and desired to be protected by Letters Patent is set forth in the appended claims:

1. A device for determining the perfusion factor of a gas carried in blood perfused in animal tissue, the device comprising, in combination, a sensor unit adapted to be placed against the animal tissue, the sensor unit including a metallic reference electrode having a flat surface adapted to be placed against the animal tissue and defining a measuring surface, a sensor electrode located at said measuring surface, means including an electrolyte establishing electrolytic contact between the metallic reference electrode and the sensor electrode, and a metallic diathermy electrode structure including a portion located at said measuring surface; polarographic measuring means connected across the reference and sensor electrodes and operative for establishing a potential difference thereacross and performing a polarographic measurement and indication of the concentration of the gas of interest; a controllable-output-power high-frequency voltage sources means having one output terminal electrically connected to the metallic reference electrode and another output terminal electrically connected to the metallic diathermy electrode structure and operative for establishing between the reference electrode and the diathermy electrode structure a high-frequency dielectric heating field operative for diathermally generating heat within dielectric constituents of the tissue against which the sensor unit is placed; means operative for sensing the temperature of the metallic reference electrode in order to detect transfer of heat from the diathermally heated tissue to the reference electrode, and in dependence upon the sensed temperature electrode, and in dependence upon the sensed temperature of the reference electrode automatically adjusting the high-frequency voltage source means to maintain the temperature of the reference electrode constant at a predetermined value; and means for indicating the heating power supplied by the high-frequency voltage source means.

2. The device defined in claim 1, the metallic diathermy electrode structure surrounding the metallic reference electrode at said measuring surface.

3. The device defined in claim 2, the metallic diathermy electrode structure surrounding the entirety of the metallic reference electrode and extending to and terminating at said measuring surface.

4. The device defined in claim 3, the device including a main unit containing said polarographic measuring means, said voltage source means, said means for sensing and adjusting, and said means for indicating, the device furthermore including a metallic tubular shield extending from the main unit to the sensor unit, the metallic shield being electrically connected to the metallic diathermy electrode structure and electrically connected to said other output terminal of said voltage source means for establishing the connection between the latter and the former, and further including conductors extending through the interior of the metallic shield and establishing the the electrical connections between the voltage source means, the polarographic measuring means and the reference and sensor electrodes.

5. The device defined in claim 4, the sensor electrode being an annular electrode comprised at least at said measuring surface of chlorided silver, the polarographic measuring means comprising means operative for performing a polarographic measurement and indication of the concentration of oxygen in perfused blood.

6. The device defined in claim 4, including a conductor establishing the electrical connection between the metallic shield and said other output terminal of said voltage source means, furthermore including tuning means connected in the conductor connecting said other output terminal and said metallic shield and tuning means connected in the conductor connecting said one output terminal of said voltage source means to said reference electrode for tuning the impedance of the conduction paths extending from the voltage source means to said measuring surface.

7. The device defined in claim 1, the voltage source means comprising means operative for establishing a diathermal heating field having a frequency of approximately 500 MHz.

8. The device defined in claim 1, furthermore including auxiliary heating means operative for supplying heat to the reference electrode.

9. A method for determining the perfusion factor of a gas carried in blood perfused in animal tissue, the method comprising, in combination, the steps of placing against the animal tissue a sensor unit comprised of a metallic reference electrode having a flat surface placed against the tissue and defining a measuring surface, a sensor electrode located at said measuring surface, means including an electrolyte establishing electrolytic contact between the metallic reference electrode and the sensor electrode, and a metallic diathermy electrode structure including a portion located at said measuring surface; connecting across the reference and sensor electrodes a polarographic measuring and indicating device and performing a polarographic measurement and an indication of the concentration of the gas of interest; connecting across the reference electrode and the diathermy electrode structure a high-frequency voltage source and establishing between the diathermy electrode structure and the reference electrode a high-frequency dielectric heating field effecting diathermal generation of heat within dielectric constituents of the tissue against which the sensor unit has been placed; using a temperature sensor to generate a signal indicating the temperature of the metallic reference electrode and using the signal to adjust the heating power output of the voltage source to maintain the temperature of the reference electrode constant at a predetermined value; and using an indicator connected to the voltage source for generating an indication of the heating power supplied by the voltage source.

* * * * *